United States Patent [19]

Crozier

[11] 4,354,980

[45] Oct. 19, 1982

[54] PROCESS FOR PRODUCING ALKYL XANTHOGEN ALKYLFORMATES

[76] Inventor: Ronald D. G. Crozier, 4 Daisy La., Ridgefield, Conn. 06877

[21] Appl. No.: 270,363

[22] Filed: Jun. 4, 1981

[51] Int. Cl.[3] .......................................... C07C 154/02
[52] U.S. Cl. ................................................ 260/455 B
[58] Field of Search ...................................... 260/455 B

[56] References Cited

U.S. PATENT DOCUMENTS 2,608,573  8/1952  Fischer ............................ 260/455 B

OTHER PUBLICATIONS

Noller, Textbook of Organic Chemistry, W. B. Saunders Co., Philadelphia, 1958, pp. 70, 128.

Reid, Organic Chemistry of Bivalent Sulfur, Chem. Publishing Co., Inc., New York, 1962, p. 134.

*Primary Examiner*—John M. Ford
*Assistant Examiner*—Robert C. Whittenbaugh
*Attorney, Agent, or Firm*—James J. Burke, II

[57] ABSTRACT

Dialkyl xanthogen formates are known collectors, but the reaction that produces them, between an alkaline alkyl xanthate and an alkaline chloroformate, also causes side reactions which produce varying amounts of xanthic anhydride, carbonyl sulfide and dialkyl carbonate as by-products, and yield of formate may be as low as 30%. There are here disclosed processing schemes for controlling the amount and type of products and by-products produced in the reaction, and flotation tests show that certain product mixtures are significantly improved collectors for sulfide ores.

8 Claims, No Drawings

PROCESS FOR PRODUCING ALKYL XANTHOGEN ALKYLFORMATES

BACKGROUND OF THE INVENTION

This invention relates to a series of collector compositions, and the processes for their production, that are useful in the froth flotation recovery of copper and molybdenum from partially oxidized sulfide ores, especially those whose clay content make them too slimy for treatment with standard reagents. The products are of general utility with other sulfide ores such as lead, zinc, silver, etc.

The structures proposed to produce the new collector formulations, whose major constituent is usually a xanthogen formate, have all been known since 1927. Alkyl xanthogen alkyl formates were disclosed by Douglass, U.S. Pat. No. 1,652,099 issued Dec. 6, 1928. Dialky xanthic anhydrides and dialkyl dixanthates were proposed in French Pat. Nos. 634,124, 634,125, and 634,126, issued in 1927 to Guggenheim Bros. These compounds have never had practical application in mining, because the recommended reagent consumption is about ten times greater than current practice. Additionally, the flotation results did not appear to justify their use.

The compounds involved in the novel formulations are:

(I) Alkyl xanthgen alkyl formates 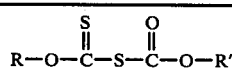

(II) Dialkyl xanthic anhydrides 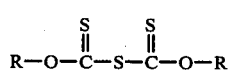

(III) Dialkoxy carbonyl sulfides 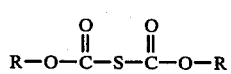

(IV) Dialkyl dixanthates 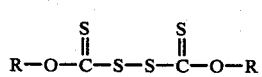

Where R and R' are straight chained, branched or substituted alkyl groups with 1 to 6 carbon atoms.

The first three of these compounds are co-products of the reaction between alkyl chloroformates and alkaline alkyl xanthates involving the following reactions:

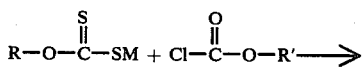 (1)

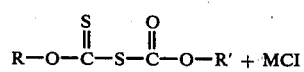

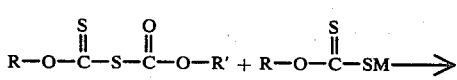 (2)

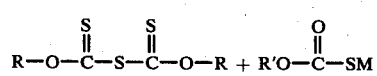

 (3)

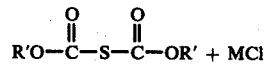

where M is an alkali metal, and R and R' are as noted above.

Compounds (II) and (III) can be produced independently in the first case by reaction (2) above, and, in the latter by the reactions:

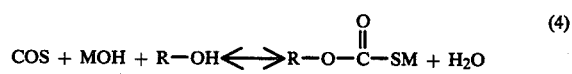 (4)

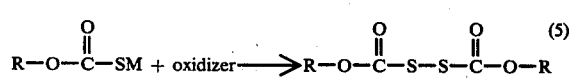 (5)

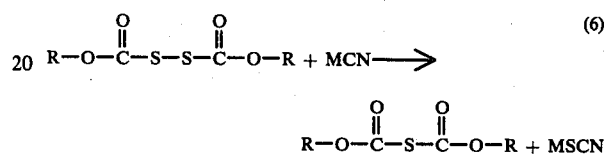 (6)

where the oxidizer can be a halogen, NaOCl, $H_2O_2$ plus acid etc.

As can be deduced from the reversibility of reaction (4), at the conditions of the reaction between a xanthate and a chloroformate, COS is given off by hydrolysis of the monothiocarbonate reducing the production of alkoxy carbonyl sulfide by reaction (3).

The effluent from reaction (6) is troublesome due to its content of alkali thiocyanate, and should be treated with acid thus:

$$MSCN + H_2O + 2H_2SO_4 \rightarrow COS + MHSO_4 + NH_4HSO_4 \quad (7)$$

recovering COS for reaction (4).

The dixanthogen, compound IV, can be produced by oxidation of the appropriate alkaline alkali xanthate:

 (8)

In the manufacture of the main xanthogen formate consumed in mining, diethyl, it has been customary to minimize by-product production of diethyl xanthic anhydride, which is a yellow solid with a melting point of 55° C., because at levels above 10 to 12% in the crude collector it causes freezing problems in storage at the mine, and when it comes out of solution the solid is essentially insoluble in water and thus does not contribute to sulfide mineral collection. Because of this, the original proposed use of xanthic anhydrides as collectors (French Pat. No. 234,125) indicated that it should be dissolved in an inert oil, such as kerosene.

The properties of the symmetrical dialkyl xanthic anhydride are:

| Alkyl Gp | Mol. Wt. | Phase | Mlt. Pt. °C. | Density $d_4^{20}$ | Refr Ind. |
|---|---|---|---|---|---|
| Dimethyl | 182.34 | Solid | 54–55 | | $n_D 25°$ |
| Diethyl | 210.34 | Solid | 52–55 | | |
| Dipropyl | 238.34 | Solid | 55 | | |
| Di-isopropyl | 238.34 | Solid | 54–55 | | |
| Dibutyl | 266.54 | Liquid | | 1.162 | 1.588 |
| Di-isobutyl | 266.54 | Liquid | | 1.126 | — |

-continued

| Alkyl Gp | Mol. Wt. | Phase | Mlt. Pt. °C. | Density $d_4^{20}$ | Refr Ind. |
|---|---|---|---|---|---|
| Diamyl | 294.54 | Liquid | | 1.107 | 1.568 |
| Dihexyl | 322.54 | Liquid | | 1.078 | 1.541 |

The solid xanthic anhydrides are useful as collectors, when dissolved in xanthogen formate solutions, as long as a compatible emulsifier is employed so that they do not come out of solution at normal flotation pulp temperatures (10°–20° C.). This metallurgical effect is shown in the flotation data of Example 7-12 below. They can also be kept in solution by the novel process of manufacturing the original ethyl xanthate, used to make the diethyl xanthogen formate, with an addition of 1 to 10% methanol to the ethyl alcohol feed.

The freezing crystallization point of different crude diethyl xanthogen formates are:

| | | Composition % | | |
|---|---|---|---|---|
| diethyl xanthogen formate | 100 | 70.5 | 62 | 52 |
| diethyl xanthic anhydride | — | 12.0 | 20 | 30 |
| diethoxy carbonyl sulfide | — | 8.4 | 8 | 8 |
| inert | — | 9.1 | 10 | 10 |
| Crystallization Temp. °C. | −36.5 | −7 | +4 | +14 |

It has been found that, without a negative effect on flotation, the addition of methanol to the original alcohol used to make xanthate will significantly lower the point of crystallization. For example 6.5 molar percent of methanol added to the original ethyl alcohol and with the reaction conditions adjusted to produce a xanthogen formate which contains 30% diethyl xanthic anhydride the crystallization point is reduced from +14° C. to 0° C. Up to 10 molar percent methanol does not adversely affect flotation properties of the collector.

OBJECTS OF THE INVENTION

A general object of the present invention is to provide a process for controlling the relative properties of reaction products in the reaction of alkaline alkyl xanthates and alkyl chloroformates.

Another object of the invention is to provide improved flotation collectors.

A more particular object of the invention is to provide a process for controlling the relative amounts of alkyl xanthogen alkyl formate, diakyl carbonate that are produced when alkaline alkyl xanthates are reacted with alkyl chloroformates.

Various other objects and advantages of the invention will become clear from the following description of embodiments, and the novel features will be particularly pointed out in connection with the appended claims.

DESCRIPTION OF EMBODIMENTS

Manufacturing process for xanthogen formates: To permit control of by-product reactions a novel manufacturing process has been developed. The procedure is as follows:

Xanthate Manufacture: The alkaline alkyl xanthate is made by known procedures, using either a high intensity agitation reactor or performing the xanthate reaction in an inert media such as benzene, toluene, xylene, hexane etc., with or without adding 1 to 10% methanol to the synthesis alcohol. The reactions are:

$$R-OH + CH_3OH + MOH \rightarrow R-OM + CH_3OM + H_2O \quad (9)$$

This reaction is exothermic and after addition of the caustic to alcohol mix it must be cooled to about 20° before adding carbon disulfide:

(10)

This reaction is carried out at a temperature which depends on the number or carbon atoms in the alkyl chain, but generally is below 50° C. The ethyl xanthate is the most sensitive to reaction conditions and is usually made with a large excess of alcohol, with the reaction temperature maintained below 35° C. Longer chain alkyl groups are normally made in suspension in an inert media, and for xanthogen formate manufacture, on completion of the xanthate reaction, the product is dissolved in water or an alcohol water mixture for transfer to the xanthogen formate reactor.

Xanthogen Formate Reaction: The conditions of this reaction are the key to the composition of the final product as at this stage reactions (1), (2), and (3) occur.

Conditions for low by-product production: In this case the xanthogen formate reactor, equipped with good agitation or an outside circulation loop equipped with a heat exchanger, is loaded with enough water to dissolve all the alkali chloride formed by reaction (1). Then, the correct amount of alkyl chloroformate is loaded into the reactor, with sufficient agitation to form a chloroformate water emulsion. The amount of chloroformate employed should be as close to equimolar to the alkyl xanthate as possible, as excess xanthate reduces yields and increases dialky xanthic anhydride production.

Xanthate preparation conditions that affect the Xanthogen formate reaction: Xanthates that are produced in suspension in an inert media normally are made using an alkyl alcohol to caustic to carbon disulfide molar ratio of (1.2 to 1.4):(1.03 to 1.07):1.0. After completion of the xanthate reaction the solid xanthate in suspension must be dissolved in deionized water, or water-alcohol solution, as soluble calcium ions are a catalyst for the production of xanthic anhydride by reaction (2). The excess alkalinity must be neutralized with an inorganic acid as OH⁻ ions reduce yield by increasing hydrolysis of the alkyl chloroformate:

$$R-O-\overset{O}{\underset{\|}{C}}-Cl + H_2O \longrightarrow R-OH + CO_2 + HCl \quad (11)$$

The excess caustic in the xanthate synthesis assures that all the CS₂ is reacted, as carbon disulfide in significant quantities is not desireable in the finished collector as it is a copper depressant. With these molar ratios, dependent on reactor agitation and temperatures employed, xanthate yields on an anhydrous basis are between 88 and 94%.

In the special case of sodium ethyl xanthate the reaction can be carried out in a great excess of ethyl alcohol with liquid caustic instead of pellets of flake, which reduce raw material costs. The excess alcohol will permit the use of up to a 5% excess of caustic without seriously affecting the chloroformate reaction. Yields, if the xanthate reaction is carried out at temperatures below 35° C., are about 94% based on carbon disulfide.

Xanthogen Formate Reaction: the main factor in the reaction between the xanthate and the chloroformate which affects side reactions is the order and rate of addition to the batch reaction. Especially with alkyl groups that form solid xanthic anhydrides at room temperature, it is essential that the xanthate solution be added to the chloroformate suspension and not vice versa, to discourage reaction (2). The rate of addition of the xanthate solution to the chloroformate is rapid at first to start the reaction, and then reduced when the reaction zone temperature reaches 35° C. The temperature must be controlled in such a manner that after completion of the addition of the xanthate solution the bulk temperature in the reactor does not exceed 56° C. Higher temperatures will increase anhydride production and reduce yields.

Higher alkyl group xanthates, whose xanthic anhydrides are liquid at room temperature, are less prone to the formation of xanthic anhydride, so that temperatures may be allowed to reach as high as 65° C. and the rate of xanthate addition is not as critical.

Conditions for high by-product production: If a xanthic anhydride content of 30% or more is desired, with diethyl xanthogen formate, addition of the chloroformate, without suspending it in water, to the xanthate solution and raising the reaction temperature will yield up to 60% of xanthic anhydride in the end product. The amount produced can be controlled by raising or lowering the reaction temperature.

Higher overall yields will be obtained. With diethyl xanthogen formate, if the first procedure, addition of the xanthate solution to the chloroformate suspension is employed and 2 to 5% $CaCl_2$, based on weight of xanthate, is added to the xanthate solution and the reaction carried out at an appropriate temperature, dependent on the amount of anhydride desired. The soluble $Ca^{++}$ ions act as a catalyst for reaction (2) and increase anhydride production. This procedure is effective with all the alkyl groups that form solid xanthic anhydrides at ambient temperatures; i.e. methyl, ethyl and propyl xanthogen ethyl formates.

For high xanthic anhydride content products based on butyl and higher xanthates it is necessary to add the chloroformate to the xanthate solution and employ soluble calcium salts in the xanthate solution as catalysts. Generally, for improved performance as a flotation collector, an anhydride content of 13 to 30% in the end product is required. To obtain this concentration in a one step synthesis from the reaction of a chloroformate with a xanthate, 20 to 30% excess xanthate must be employed, which significantly reduces yields, so that the independent production of the xanthic anhydride by reacting the corresponding xanthogen formate with xanthate (equation 2) or the independent synthesis of the anhydride by removing a sulfur atom by the reaction of a dixanthate with an alkali cyanide, may be a more economic route.

Up to 60% xanthic anhydride content can be obtained with $C_4$ or higher alkyl xanthates if first, an equimolar quantity of ethyl chloroformate is added to a xanthate solution, containing 2 to 5% $CaCl_2$, decanting the oily crude product and dissolving it in acetone, and reacting about 0.5 moles of the same xanthate solution with the equivalent of 1.0 moles of the reaction product while refluxing the acetone solution. The reaction product, after washing with water to remove the acetone, will contain about 60 to 70% xanthic anhydride, 10% dialkoxy carbonyl sulfide and the balance xanthogen formate. The acetone may be recovered from the wash water by salting out.

The following specific examples of laboratory preparations show the effect of employing $Ca^{++}$ ions as a catalyst to enhance by-product formation in the xanthate chloroformate reaction, and reference thereto will enhance understanding of the invention.

EXAMPLE 1

In a three necked flask equipped with external cooling and good agitation 100 ml of water are placed and 54 gm of ethyl chloroformate are slowly added, with agitation, to make a uniform suspension of chloroformate in water. To this suspension 86.1 gm of sodium isobutyl xanthate dissolved in 250 ml of water are slowly added while maintaining the temperature below 40° C. and continuing with strong agitation. After completion of the addition of the xanthate solution stirring is continued for 30 minutes, the oily phase is then decanted and washed with water and dried with anhydrous sodium sulfate. The crude product weighed 90.8 grams.

EXAMPLE 2

In a similar three necked flask 85 gm of the product of reaction in Example 1 are placed and heated to 40° C. To this a 30% aqueous solution containing 80 gm of sodium isobutyl xanthate are added and agitated for 2 hours, until no more gas (COS) is evolved. The oily product is decanted, washed with water and dried with anhydrous sodium sulfate. The crude product weighed 93 gms.

EXAMPLE 3

The above experiment was repeated adding 2 gm of $CaCl_2$ to the xanthate solution, which became turbid. On addition of the xanthate solution to the product of reaction in Example 1 there was more vigorous evolution of gas. The crude product was washed with water and dried, it weighed 108 gm.

EXAMPLE 4

Example 3 was repeated but the xanthate was dissolved in 200 gm of acetone and 2 gm of $CaCl_2$ were placed in the bottom of the flask with the xanthogen formate. The reaction was carried out refluxing the acetone, gas evolution was lower than in Example 3. At the end of the reaction the acetone was extracted with water, with some evolution of gas, and the oily product washed and dried. The yield was 115 gm. The water phase contained unreacted xanthate and monothiocarbonate was detected.

EXAMPLE 5

The reaction with ethylchloroformate was repeated as in Example 1 with the additon of 2 gm of $CaCl_2$ to the xanthate solution. The final yield was 88 gms.

The products of these reactions were analyzed by gas chromatography, with the following results:

| Example Composition % | 1 | 2 | 3 | 4 | 5 |
|---|---|---|---|---|---|
| Isobutyl xanthogen formate | 84.1 | 77.7 | 51.7 | 36.8 | 62.1 |

-continued

| Example Composition % | 1 | 2 | 3 | 4 | 5 |
|---|---|---|---|---|---|
| Isobutyl xanthic anhydride | 8.6 | 15.2 | 38.2 | 57.4 | 21.4 |
| Diethoxy carbonyl sulfide | 4.3 | 4.2 | 3.6 | 3.4 | 12.0 |
| Inerts | 3.0 | 2.9 | 2.5 | 2.4 | 4.5 |
| Yield, gms | 90.8 | 93.0 | 108.0 | 115.0 | 88.0 |

EXAMPLE 6

In a three necked flask equipped with a stirrer, thermometer, cooling and a submerged glass tube equipped with a three way stop clock, 88 ml (1.5 moles) of ethyl alcohol was placed and 40 gm (1.0 moles of NaOH, dissolved in 50 ml of water, was slowly added to the alcohol with cooling. After the temperature was steady at 20° C., 24 liters (1.0 moles) of COS gas was slowly bubbled into the alcoholate mix, while keeping the reaction mix at less than 25° C. The COS was measured with a positive displacement meter.

After completion of the addition of the COS, the same entry tube was employed to add 100 gm (0.92 moles) of ethyl chloroformate, maintaining vigorous stirring and cooling to keep the temperature of the reaction mix under 30° C. On completion of the addition of the ethyl chloroformate, stirring was continued for 1 hour. The oily reaction product was decanted and thoroughly washed with excess water then dried with anhydrous sodium sulfate. The yield was 163 gm which on gas chromatographic analysis showed:

| Diethoxy carbonyl sulfide | 92% |
|---|---|
| Diethyl carbonate | 2% |
| Ethyl alcohol | 6% |

This corresponds to a yield of 85% on COS and 92% on ethyl chloroformate.

Improved metallurgical collector formulations: All components of crude alkyl xanthogen alkyl formates are metallurgically active, this characteristic can be maximized by the versatility of the new processes described. The following example is illustrative:

EXAMPLES 7–12

A porphyry mineral, low in clays and with a normal oxide content (non-sulfides), whose total copper content was 1.48% and molybdenum 0.013% was floated a 19° C. and at a pH of 4.0 for 7 minutes with the standard collector composition in use in the mine as a comparison (test 7). The collector was formulated as a 60% solution in 30% gasoline and 10% methyl isobutyl carbinol (MIBC), normal procedure for the mine from which the ore was obtained.

Feed to the flotation cell was:

| Collector mix | 80 grams/Ton of mineral |
|---|---|
| Frother, Dowfroth 1012 | 40 grams/Ton of mineral |
| Fuel Oil | 20 grams/Ton of mineral |
| Sulfuric Acid | 2000 grams/Ton of mineral |

The collector composition employed in preparing the mix and the results of flotation tests in a laboratory Wemco machine operated at 1,600 rpm were:

| Example | Collector Composition % | | | | | |
|---|---|---|---|---|---|---|
| | 7 | 8 | 9 | 10 | 11 | 12 |
| Ethyl xanthogen Ethyl Formate | 70.1 | 100 | 51.2 | 51.2 | 60 | — |
| Isobutyl xanthogen Ethyl Formate | — | — | 13.7 | 13.7 | — | — |
| Diethyl Xanthic Anhydride | 12.0 | — | 15.0 | — | — | — |
| Diethyl Xanthic Anhydride (emulsified) | — | — | — | 15.0 | — | — |
| Diethoxy Carbonyl Sulfide | 8.4 | — | 8.9 | 8.9 | 40 | 100 |
| Inerts | 9.1 | — | 11.2 | 11.2 | — | — |

Flotation results were as follows:

| | CONCENTRATE | | | TAILS | | | RECOVERIES | |
|---|---|---|---|---|---|---|---|---|
| Test | Wgt grm | % CuT | % MoT | Wgt grm | % CuT | % MoT | % CuT | % MoT |
| 7 | 101.0 | 12.77 | 0.106 | 890.0 | 0.21 | 0.0024 | 87.3 | 83 |
| 8 | 87.3 | 14.89 | 0.122 | 914.0 | 0.20 | 0.0025 | 87.7 | 82 |
| 9 | 89.6 | 14.36 | 0.117 | 908.0 | 0.21 | 0.0027 | 87.1 | 81 |
| 10 | 87.0 | 14.76 | 0.140 | 909.0 | 0.21 | 0.0008 | 87.1 | 94 |
| 11 | 90.0 | 14.37 | 0.135 | 913.0 | 0.20 | 0.0010 | 87.6 | 93 |
| 12 | 79.0 | 14.04 | 0.152 | 944.0 | 0.39 | 0.0013 | 75.1 | 91 |

As can be seen from comparing Test 7 and 8 there is no significant difference in flotation efficiency between a pure distilled diethyl xanthogen formate and a normal commercial purity; there is also no effect when the xanthic anhydride content is raised from 12 to 15% if the anhydride can come out of solution at the flotation temperature. If an emulsifier, such as a sulphonated coconut oil or methanol is added to the original xanthate, the xanthic anhydride does not come out of solution and by comparing test 9 and 10 one sees a strong improvement in molybdenum recovery. Copper recovery was not affected in any of the tests because the ore was not slimey. Tests 11 and 12 show that diethoxy carbonyl sulfide is also a very good molybdenum collector, but not so for copper.

The effect of collector composition on the flotation of slimes containing, partially oxidized ores, is shown in the next series of examples:

EXAMPLES 13–15

In this series of laboratory flotation tests a high clay content ore, from the same mine as in Examples 7–12 were employed at the same test conditions. The ore treated had copper heads of 1.45%, of which 0.36% was non-sulfide mineral, and a molybdenum content of 0.015%. The flotation results were:

| | Collector Composition | | |
|---|---|---|---|
| Example | 13 | 14 | 15 |
| Ethyl Xanthogen Ethyl Formate | 70.5 | 49.9 | 47.3 |
| Isobutyl Xanthogen Ethyl Formate | — | 13.4 | 12.8 |
| Diethyl Xanthic Anhydride | 12.0 | 11.0 | 10.4 |
| Diethoxy Carbonyl Sulfide | 8.4 | 15.0 | 20.0 |
| Inerts | 9.1 | 10.7 | 9.5 |
| Flotation Results | | | |
| Total Copper Recovery % | 85.3 | 86.8 | 87.5 |
| Total Molybdenum Recovery % | 76 | — | 83 |

In this series of tests one can see that increasing the content of diethoxy carbonyl sulfide significantly improves both copper and molybdenum recovery in the presence of clays and that an increase in the longer chain alkyl xanthogen ethyl formate improves copper recovery.

The next examples show the effect of methanol addition to the xanthate used in preparing the xanthogen formate on the crystallization temperature of the xanthic anhydride.

EXAMPLES 16-19

The temperature at which crystals of xanthic anhydride appear as a function of the xanthic anhydride content of a crude xanthogen formate collector is:

|  | Composition % | | | |
|---|---|---|---|---|
| Example | 16 | 17 | 18 | 19 |
| Ethyl Xanthogen Ethyl Formate | 100 | 70.5 | 62 | 52 |
| Diethyl Xanthic Anhydride | — | 12.0 | 20 | 30 |
| Diethoxy Carbonyl Sulfide | — | 8.4 | 8 | 8 |
| Inerts | — | 9.1 | 10 | 10 |
| Crystallization Temperature °C. | −36.5 | −7 | +4 | +14 |

If 6.5% molar methanol is added to the original ethyl alcohol employed in the synthesis of ethyl xanthogen ethyl formate and the reaction conditions are adjusted to produce a final product with 30% diethyl xanthic anhydride, the crystallization point is reduced from +14° C. to 0° C. Up to 10% methanol may be added without adversely affecting flotation; on the contrary, the diethyl xanthic anhydride acts as if it had been emulsified. The exact compound which acts as a solubilizer has not been determined.

The use of liquid dialkyl xanthic anhydrides and dialkyl dixanthogens in collector formulations: The addition of soluble liquid dialkyl xanthic anhydrides and dixanthogens significantly improves the flotation characteristics of xanthogen-formate type collectors.

The properties of the dialkyl dixanthates of increased chain lengths are:

| Dixanthate | Phase | Melt. Pt °C. | Density $d_4^{20}$ | Refr. Inc. |
|---|---|---|---|---|
| Dimethyl | solid | 23–23.5 | 1.381 a 30° | 1.672 |
| Diethyl | solid | 31.5–32 | 1.265 a 35° | — |
| Dipropyl | liquid(?) | (?) | 1.208 | 1.607 |
| Di-isopropyl | solid | 57–59 | — | — |
| Dibutyl | liquid | — | 1.156 | 1.581 |
| Di-isobutyl | liquid | — | 1.080 | — |
| Diamyl | liquid | — | 1.119 | 1.570 |
| Dihexyl | liquid | — | 1.090 | 1.558 |

EXAMPLES 20-22

A series of flotation tests were run employing xanthogen formate collectors with increased contents of liquid xanthic anhydrides and dialkyl dixanthogens. The compositions of the collectors employed were:

| Example Collector # | 20 | 21 | 22 |
|---|---|---|---|
| % Ethyl Xanthogen Ethyl Formate | 70.5 | 38.4 | 38.4 |
| % Isobutyl Xanthogen Ethyl Formate | — | 10.3 | 10.3 |
| % Diethyl Xanthic Anhydride | 12.0 | 8.5 | 8.5 |
| % Diethoxy Carbonyl Sulfide | 8.4 | 11.5 | 11.5 |
| % Di-isobutyl Xanthic Anhydride | — | 20.2 | — |
| % Di-isobutyl Dixanthogen | — | — | 20.2 |
| % Inerts | 9.1 | 9.4 | 9.4 |

A laboratory flotation was carried out in a standard "Wemco" flotation machine, employing 1,000 gm ore samples ground in a laboratory ball mill. A difficult ore, from a Chilean porphyry copper mine, with a total copper content of 1.08%, of which 0.28% was non-sulfide, and with a high clay content was employed in the first test.

The flotation test conditions were as follows:

| | |
|---|---|
| Reagents and dossage: | |
| Frother, Dowfroth 1012 | 40 gms/metric ton ore |
| Supplementary Collector, Potassium amyl xanthate | 20 gms/metric ton ore |
| pH control, Lime | 1000 gms/metric ton ore |
| Test Collector | 48 gms/metric ton ore |
| Flotation conditions: | |
| Conditioning time | 3 minutes |
| Flotation time | 8 minutes |
| Mineral Grind (Tyler) | 45% − 200 mesh |
| | 17% + 65 mesh |

| Flotation Results: | | | |
|---|---|---|---|
| Collector Sample # | 20 | 21 | 22 |
| Concentrate | | | |
| Weight, gm | 135 | 139 | 139 |
| % total Copper | 6.3 | 6.1 | 6.4 |
| Tails | | | |
| Weight, gm | 865 | 861 | 861 |
| % total Copper | 0.29 | 0.23 | 0.23 |
| Calculated Head % Cu | 1.10 | 1.05 | 1.09 |
| Recovery | | | |
| % total Copper | 72.2% | 81.1% | 81.8% |

As can be seen the increase in either di-isobutyl xanthic anhydride content or the di-isobutyl dixanthogen content is significantly improved copper recovery from this difficult-to-float ore, as can be inferred from the low recovery with the standard reagent in use in the mine, Collector composition 20.

EXAMPLES 23-25

A second ore sample from a different sector of the same mine as the ore employed in Example 6, with a lower clay content, and with 1.44% total copper of which 0.30% was nonsulfide, was tested under the same flotation conditions employed in the previous example, except that 2,000 gm/metric ton of ore of lime was used. Under these conditions the flotation results were:

| Collector Example # | 20 | 21 | 22 |
|---|---|---|---|
| Concentrate | | | |
| Weight, gm | 136 | 129 | 127 |
| % total Copper | 9.3 | 10.2 | 9.8 |
| Tails | | | |
| Weight, gm | 864 | 871 | 873 |
| % total Copper | 0.27 | 0.23 | 0.23 |
| Calculated Head, % Cu | 1.49 | 1.51 | 1.44 |
| Recovery | | | |
| % total Copper | 84.4% | 86.8% | 86.1% |

EXAMPLES 26-29

A third ore sample from the same mine, with intermediate flotation characteristics, and a copper head of 1.18% was tested under the same general conditions as used in Examples 20-25, except both the frother and test collector dossage was increased to 60 gm/metric ton of ore. One test was performed at the natural pH of the ore by omitting the addition of lime, the rest were performed with 2,000 gm of lime/metric ton of ore.

The flotation test results were the following:

|  | 20 | 21 |
|---|---|---|
| Collector Example # | | |
| Concentrate | | |
| Weight, gm | 112.3 | 137.5 |
| % total Copper | 11.02 | 9.23 |
| % total Molybdenum | 0.102 | 0.090 |
| Collector sample # | | |
| Tails | | |
| Weight, gm | 887.7 | 862.5 |
| % total Copper | 0.24 | 0.21 |
| % non-sulfide Cu | 0.16 | 0.15 |
| % total Molybdenum | 0.004 | 0.003 |
| Recoveries | | |
| % total Copper | 85.3% | 87.5% |
| % total Molybdenum | 76.0% | 82.7% |

As can be seen from these results, a liquid xanthic anhydride incorporated into a xanthogen formate base has a similar effect on improving molybdenum recovery as in the case of emulsified solid xanthic anhydrides as shown in Examples 7-12. Diethoxy carbonyl sulfide is also liquid at room temperature and also shows a marked improvement in molybdenmum recovery. The ore employed in Examples 7-12 was easily floated so there were no significant effects on copper recovery. The ore used in these examples was a relatively poor floating type and in this case both the liquid xanthic anhydrides and dixanthogens show improved handling of clay containing ores.

Various changes in the details, steps, materials and arrangements of parts, which have been herein described and illustrated in order to explain the nature of the invention, may be made by those skilled in the art, within the principle and scope of the invention as defined in the appended claims.

What is claimed is:

1. In a process for producing alkyl xanthogen alkyl formates by reaction of an alkaline alkyl xanthate and an alkyl chloroformate according to the generalized reaction:

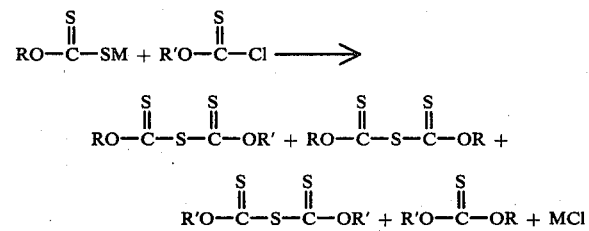

where R and R' are selected from the group consisting of linear, branched and substituted alkyl groups with one to six carbon atoms and M is an alkali metal, the improvement comprising:
adding soluble calcium salt to an aqueous xanthate solution to provide 2-5% Ca++ by weight as CaCl$_2$ compared to xanthate;
adding to said xanthate solution said chloroformate in proportion of 1 mole chloroformate to 1-2 moles xanthate; and
maintaining the reaction temperature in the range of 35° to 60° C., depending on the size of the xanthate alkyl group;
whereby the amount of dialkyl xanthic anhydride produced as a by-product may be controlled within the range of 13-60%.

2. In a process for producing alkyl xanthogen alkyl formates by reaction of an alkaline alkyl xanthate and an alkyl chloroformate according to the generalized reaction:

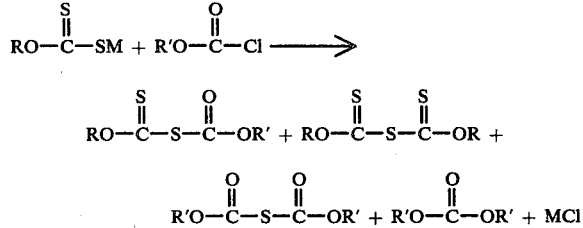

where R and R' are selected from the group consisting of linear, branched and substituted alkyl groups with one to six carbon atoms and M is an alkali metal, the improvement comprising:
forming a water emulsion of said alkyl chloroformate;
reacting said chloroformate emulsion with an aqueous xanthate solution under conditions of agitation; and
maintaining the reaction temperature between 30° and 60°;
carrying out said reaction in the presence of calcium ions in an amount equivalent to 2-5% of the weight of xanthate of CaCl$_2$;
whereby, depending on temperature, dialkyl xanthic anhydride in the reaction product is controlled between 13 and 25%.

3. In a process for producing alkyl xanthogen alkyl formates by reaction of an alkaline alkyl xanthate and an alkyl chloroformate according to the generalized reaction:

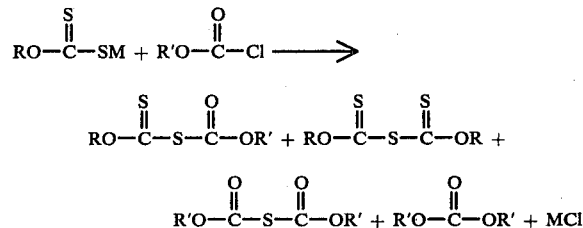

where R and R' are selected from the group consisting of linear, branched and substituted alkyl groups with one to six carbon atoms and M is an alkali metal, the improvement comprising:
carrying out said reaction in the presence of calcium ions in an amount equivalent to 2-5% of the weight of xanthate of CaCl$_2$.

4. The process as claimed in claim 3, and additionally comprising adding acetone to the reaction mixture as a cosolubilizer.

5. The process of producing dialkoxy carbonyl sulfide by reacting an alkyl monothiocarbonate with an alkyl chloroformate:

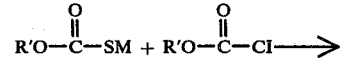

-continued

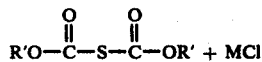

R, R' and M being defined as in claim 3, and wherein said alkyl monothiocarbonate is obtained as a by-product of the process of claim 3.

6. The process as claimed in claims 1 or 2, wherein R' is selected from the group consisting of methyl and ethyl.

7. The process as claimed in claims 1 or 2, wherein M is selected from the group consisting of sodium and potassium, and R is selected from the group consisting of ethyl, isobutyl, and mixtures of ethyl and isobutyl.

8. The process as claimed in claim 7, wherein R is a mixture of 80% ethyl and 20% isobutyl, and R' is ethyl.

* * * * *